United States Patent [19]
Parekh

[11] Patent Number: 6,024,945
[45] Date of Patent: Feb. 15, 2000

[54] ANTIPERSPIRANT COMPOSITIONS FOR AEROSOL FORMULATIONS

[75] Inventor: Jawahar Chunilal Parekh, Livingston, N.J.

[73] Assignee: Reheis, Inc., Berkeley Heights, N.J.

[21] Appl. No.: 09/363,356

[22] Filed: Jul. 29, 1999

[51] Int. Cl.⁷ .............. A61K 7/38; A61K 7/32; A61K 7/00
[52] U.S. Cl. .............. 424/68; 424/65; 424/400; 424/401
[58] Field of Search .................. 424/65, 66, 67, 424/68, 400, 401

[56] References Cited

U.S. PATENT DOCUMENTS 4,675,356  6/1987  Miyata .................... 524/424
5,718,876  2/1998  Parekh .................... 423/462

*Primary Examiner*—Shelley A. Dodson
*Attorney, Agent, or Firm*—Arthur J. Plantamura; Birgit E. Morris

[57] ABSTRACT

The formation of toxic compounds such as acetaldehyde and monochlorofluoroethane generated by aerosol antiperspirant mixtures of ACH and 1,1-difluoroethane can be substantially reduced by the addition of one or more additives. Such additives include amino acids, their alkali metal, alkaline earth, ammonium and hydroxy aluminum salts, metal glycinates, hydrotalcite or analogues thereof, and complex aluminum buffering agents. The resultant mixtures are stable for at least two years under ambient storage conditions.

19 Claims, 4 Drawing Sheets

ANTIPERSPIRANT COMPOSITIONS FOR AEROSOL FORMULATIONS

This invention relates to improved aerosol antiperspirant compositions. More particularly, this invention relates to aerosol antiperspirant compositions that are stable to long term storage and essentially non-corrosive to metal containers.

BACKGROUND OF THE INVENTION

Basic aluminum halides, particularly the chlorides, also referred to as aluminum chlorohydroxides, aluminum sesquichlorohydrate, aluminum dichlorohydrate and the like, as well as aluminum nitrates, have been known and used for years as effective antiperspirants. They constitute the essential active ingredient in many currently marketed antiperspirants.

In general, basic aluminum halides and nitrates are complex structures comprised of mixtures of polymeric and monomeric compounds having various sizes and molecular structures, together with varying amounts of bound or coordinated water. They can be represented by the empirical formula $Al_2(OH)_{(6-x)}y_x$, wherein x is between 0 and 6 and need not be an integer, and y is one or more of the group including chloride, bromide, iodide or nitrate ions. The empirical formula is simplified and is intended to include basic aluminum chlorides containing coordinated or bound molecules of water, as well as basic aluminum chloride polymers, complexes and mixtures thereof.

Particularly preferred compounds are aluminum chlorohydrates in which x is about 1 to 2, and most preferably x is about 1, the latter being referred to as 5/6 basic aluminum chloride. Such compounds have an Al:Cl mol ratio of about 1:1 to 2.1:1, and preferably a mol ratio of from 1.9:1 to 2.1:1.

The 5/6 basic aluminum chloride (hereinafter referred to as ACH) has been recognized as the standard active ingredient for antiperspirants for many years. It has been available in various forms, typically in 50 weight percent aqueous solution (commercially available from Reheis Chemical Company under the trademark "Chlorohydrol®") or in dry form obtained by spray drying aqueous solutions to some extent, but which does not remove all of the bound or coordinated water. These dry forms are available in different particle sizes. They are also referred to as "activated ACH" or "enhanced efficacy ACH". In addition, these compounds may be co-dried or otherwise combined with any of a number of adjuvants and/or additives designed to perform various functions, such as moieties of propylene glycol, polyethylene glycol and the like.

Basic aluminum compounds have been formulated with various materials to form aerosol spray-type antiperspirants, as well as formulations for pump sprays, creams, sticks, roll-ons and the like.

Aluminum chlorohydrates, hereinafter designated with the generic term "ACH", are the only active antiperspirants deemed safe and effective by the Federal Drug Administration for use in aerosol antiperspirant products.

The propellants used for forming aerosol-type antiperspirants up till now have been highly volatile organic compounds (HVOC), such as fluorocarbons, known collectively as Freon. However, since these fluorocarbons are believed to deplete the earth's ozone layer, the Federal Government has banned the use of Freon. Each state must outline plans for implementation of the current guidelines and set a date for compliance. The California Air Resource Board (CARB) has proposed that high volatility organic compounds (HVOC), i.e. compounds that exert a vapor pressure greater than 80 mm Hg at 20° C., be 0%, and that medium volatility organic compounds (MVOC), i.e. compounds that exert a vapor pressure greater than 2 mm Hg at 20° C., be 10% by Jan. 1, 2001.

Because CARB had originally mandated compliance with the above standards by Jan. 1, 1999, various manufacturers of antiperspirant aerosols attempted to switch from fluorocarbons to a mixture of ACH and 1,1-difluoroethane.

1,1-Difluoroethane has no chlorine atoms, and thus is not of concern regarding stratospheric ozone destruction by chlorofluorocarbons or other chlorinated hydrocarbons. It has an ozone Depletion Potential of zero, and the Environmental Protection Agency (EPA) has found that it is not a VOC.

Unfortunately, however, ACH and 1,1-difluoroethane react with each other over time, particularly at elevated temperatures. This reaction produces 1-chloro-1-fluoroethane (replacing one of the F ions with a Cl ion), hereinafter referred to as monochlorofluoroethane, and acetaldehyde as by-products. Acetaldehyde is classified as a toxic compound by CARB and as a hazardous air pollutant by the EPA. Further, the reaction between 1,1-difluoroethane and ACH also results in corrosion of metal containers, such as those used to store aerosol products, and in the deterioration of the valve component of the containers.

The mechanisms of these reactions is not known with certainty, or whether the generation of these by-products takes place separately or whether one leads to the other. However, their presence in the above compositions can be measured.

Thus ACH and 1,1-difluoroethane cannot be used together by themselves in antiperspirant aerosol compositions, and a search for a means of inhibiting the formation of the acetaldehyde by-product from the above combination for a period of about two years at room temperature was initiated.

SUMMARY OF THE INVENTION

I have found that the reaction between 1,1-difluoroethane and ACH that produces toxic compounds such as monochlorofluoroethane and acetaldehyde, and corrodes metal containers, can be greatly reduced or blocked by the addition of one or more additive compounds, which additives can include an amino acid, an amino acid compound which may be an alkali metal, alkaline earth metal, ammonium or hydroxy salt of an amino acid; or a metal glycinate, a hydroxy aluminum salt of an amino acid; hydrotalcite and hydrotalcite analogues; complex aluminum buffering agents; and aluminum or magnesium based antacids and alkali metal salts thereof, to the mixture of ACH and 1,1-difluoroethane. The resultant compositions of ACH, 1,1-difluoroethane and additive are stable. They can be stored for about two years or more at room temperature with small, or even non-detectable, levels of generated acetaldehyde and of monochlorofluoroethane.

I have found that using 1,1,-difluoroethane alone, aerosol cans did not corrode at room temperature. Combinations of 1,1-difluoroethane and ACH produce undesirable by-products at elevated temperatures, independent of the water content and acidity of the ACH, and cause detinning and corrosion of aerosol cans.

DETAILED DESCRIPTION OF THE INVENTION

The three key factors affecting the formation of undesirable by-products in the above compositions are the acidity of the ACH, the presence of water, either released from the ACH or formed as a result of other reactions taking place, and the storage temperature. The rate of formation of these undesirable reactions is much higher at elevated temperatures; for example, the reaction rate is about 20 times higher at 120° F. than at 70° F. Concomitantly, the rate of corrosion of metal parts is also higher at elevated temperatures.

Chlorohydrol solution (ACH) is a complex inorganic polymer. It is made of mixtures of polymeric and monomeric species of various sizes and molecular structures, together with varying amounts of bound or co-ordinated water.

I have found that the addition of various additives, including a glycine compound, or a halogen scavenger such as hydrotalcite, inhibits the reactions between ACH and 1,1-difluoroethane.

ACH contains varying water levels, depending on how the ACH is prepared. ACH is a hygroscopic material and water absorption in the handling and product manufacturing processes can influence the amount of water contained in the finished aerosol. The atomic ratio of Al:Cl can vary from 2.1:1 to 1.0:1. This ratio in turn affects the acidity and other characteristics of ACH. The particle size and particle size distribution may be another important variable, because it affects the surface area available to influence reaction rates and reaction mechanisms. Since activated ACH has a higher acidity and includes more reactive species, it was chosen for testing the concept of minimizing the formation of undesirable by-products, particularly acetaldehyde and monochlorofluoroethane, as by buffering with an amino acid compound.

In addition to amino acids per se, such as glycine, compounds thereof that are useful herein include alkali metal and alkaline earth metal salts of amino acids, as well as ammonium or hydroxy salts of amino acids.

As used herein, the term "alkaline" as applied to salts of amino acids, is not intended to be limited to those having a pH greater than 7.0, since some complex or imperfectly neutralized salts can have a pH less than 7.0 and still be useful in this invention. Instead, alkaline is meant to refer to the usual alkali and alkaline earth metal cations, including ammonium and hydroxy.

Metal glycinates such as sodium or zinc glycinate can also be used. Among the salts of amino acids useful herein are those derived from amino acids in which the number of amino groups is equal to the number of carboxyl groups in the molecule. Examples of such amino acids include glycine, DL-valine, beta-alanine, arginine, and L(-) prolinates. Suitable salts of other amino acids are useful in the present invention as will be evident to those skilled in the art. It is important to note that water-insoluble as well as soluble salts can be used.

Suitable hydroxy salts of amino acids useful herein include the monohydroxy and dihydroxy aluminum salts of amino acids, and aluminum-magnesium-hydroxy-glycine compounds, such as monohydroxy aluminum glycinate, magnesium glycinate and calcium glycinate. These hydroxy salts are the reaction products of aluminum hydroxy antacids and the desired amino salt. Since these glycinates are available in different basicities, the amount of glycinate or other salt to be used depends upon the particular basicity of the amino salt. In general, about 0.5 to 15% by weight of the above salts will be used with ACH, but the desirable amount will depend on the formulation and the active antiperspirant used.

Other compounds useful herein include aluminum hydroxy carbonate, magnesium carbonate, magnesium hydroxide and complex aluminum buffering compounds containing, in addition to aluminum, two or more of the following: magnesium, calcium, sodium, carbonate, sulfate, hydroxyl and water. The complex aluminum buffer preferably contains magnesium and/or carbonate. Suitable complex aluminum buffers include antacid complexes such as co-precipitates or co-dried mixtures of aluminum hydroxide with magnesium carbonate and/or calcium carbonate, dihydroxy aluminum sodium carbonate, tetrahydroxy dialuminum magnesium carbonate, hydrated magnesium aluminate, hydrated magnesium aluminum sulfate, aluminum magnesium hydroxy sulfate, aluminum hydroxy carbonate, magnesium hydroxide and the like.

A dry blend of hydrotalcite and activated ACH will also reduce the formation of acetaldehyde in the present compositions because any free chloride or fluoride will be permanently bound. Hydrotalcite occurs naturally, but is generally contaminated with other minerals and heavy metals, which limits its usefulness. However, high purity hydrotalcite can be prepared synthetically, as is well known. Synthetic hydrotalcite ($Mg_6Al_2(OH)_{16}CO_3 4H_2O$) has a substantial anion exchange property. For example, the carboxylic acid radical of hydrotalcite is easily ion exchanged by chloride ion, which is adsorbed and fixed in a stable crystal structure. The resulting compound is insoluble in water, and stable; a temperature of about 450° C. is required to release chloride ion from the structure.

The term "hydrotalcite" is often used generically to refer to a large class of basic aluminum magnesium carbonate compounds or complexes having various lattice structures and compositions. These hydrotalcite-like materials are also referred to as hydrotalcite analogues. Hydrotalcite can be represented by the following general formula:

$$M^{2+}_{1-x}M_x^{3+}(OH)_2 A_{x/n}^{n-} \cdot mH_2O$$

wherein x is greater than zero but less than or equal to 0.5; m is a positive number; $A^{n-}$ is an anion having a valence of n; $M^{2+}$ is one or more metal ions selected from the group consisting of Be, Mg, Ni, CO, Zn, Fe, Mn, Cd and Ca; and $M^{3+}$ is one or more metal ions selected from the group consisting of Al, Ga, Ni, Co, Fe, Mn, Cr, and In; $An^{n-}$ is an anion selected from the group consisting of $SO_4^=$, $OH^-$, $CO_3^=$ and $(HPO_4)$ and the like. Two or more anions can be included, when x/n is the total value of two or more anions.

Hydrotalcite may also be represented by the following formula, as described in U.S. Pat. No. 4,675,356 to Miyata:

$$(M_1^{2+})_{y1}[(M_2^{2+})_{y2}]_{1-x}M^{3+}_x(OH)_2 A_{x/n}^{n-} \cdot mH_2O$$

wherein $M_1^{2+}$ is at least one divalent metal cation selected from the group consisting of Mg, Ca, Sr and Ba; $M_2^{2+}$ is at least one divalent metal cation selected from the group consisting of Zn, Cd, Pb and Sn, $M^{+3}$ is a trivalent metal cation which can be trivalent aluminum; $A^{n-}$ is an anion having a valence of n; and x, $y_1$, $y_2$ and m are positive numbers having the following values: x is greater than zero and less than 0.5; $y_1$ is greater than zero; $y_2$ is greater than zero; $(y_1+y_2)$ is greater than 0.5 and less than 1; and m is greater than zero and less than 2.

In order to test the levels of acetaldehyde formation, the following test procedure was used. Samples of enhanced efficacy ACH powder were blended with 1,1-difluoroethane in a ratio of 1:5 by weight concentration in glass bottles including metal coupons (representing the can). The samples were sealed and stored at 120° F. The metal coupons were exposed to the solid, liquid and vapor phases, so that corrosion in each phase could be visually observed. Samples were withdrawn from the vapor phase and analyzed using a gas chromatograph with a mass spectrophotometer and a flame ionization detector and the surface conditions of the metal coupon were visually observed in the vapor phase, the liquid phase (propellant phase) and the solid phase (ACH). This procedure was repeated at periodic intervals.

The compositions of the invention and method of making them will be further described in the following examples, but it is to be understood that the invention is not meant to be limited to the details described therein. In the Examples, percent (%) is by weight.

EXAMPLE 1

16,000 Grams of an enhanced efficacy ACH solution containing 3.11% of aluminum and 2.13% of chloride was prepared.

One half of the resulting solution was spray dried using a 30" diameter conical bottom Bowen spray dryer having an outlet temperature of 230° F. The resultant powder was micronized using an air jet mill until about 95% of the product passed through a 325 mesh screen. This sample is designated as Control 1.

44 Grams of glycine was added to the second half of the solution. The resultant solution was refluxed for one hour and spray dried at an outlet temperature of about 195–205° F. This product was micronized until about 97% of the product passed through a 325 mesh screen, and is designated as Example 1. The chemical analysis of the Control and Example 1 is summarized in Table I.

TABLE I

| Sample | % Al | % Cl | Al:Cl | Fe,ppm |
| --- | --- | --- | --- | --- |
| Control 1 | 24.57 | 16.75 | 1.93:1 | 75 |
| Example 1 | 23.76 | 16.49 | 1.89:1 | 77 |

Control 1 and Example 1 were mixed with 1,1-difluoroethane at a 20% concentration in glass bottles and stored at 120° F. Metal coupons were added to represent the aerosol can. The reaction by-products for each of the samples were measured in the vapor phase using gas chromatography. The samples were analyzed after storage for various periods of time as shown in Table II.

TABLE II

| | Weeks | | | | | | | | |
| --- | --- | --- | --- | --- | --- | --- | --- | --- | --- |
| Sample | 1 | 3 | 5 | 7 | 9 | 11 | 15 | 21 | 29 |
| Acetaldehyde | | | | | | | | | |
| Control 1 | 4.6 | 11.9 | 17.5 | 30.7 | 40.9 | 56.4 | 44.5 | 109.5 | 127.9 |
| Example 1 | 1.1 | 3.6 | 4.7 | 6.8 | 7.1 | 13.2 | 14.7 | 39.3 | 49.1 |
| Monochlorofluoroethane | | | | | | | | | |
| Control 1 | 18.6 | 48.4 | 74.7 | 127.2 | 172.2 | 239.5 | 181.9 | 476.4 | 553.9 |
| Example 1 | 4.1 | 13.6 | 19.9 | 30.3 | 31.8 | 45.3 | 65.9 | 172.7 | 205.3 |

Table II shows that after storing for 11 weeks, Control 1 contained 56.4 ppm of acetaldehyde and 239.5 ppm of monochlorofluorethane, whereas the composition of Example 1 contained only 13.2 ppm of acetaldehyde and 45.3 ppm of monochlorofluoroethane, a 77% reduction in acetaldehyde and an 81% reduction in monochlorofluroethane.

EXAMPLES 2 AND 3

Two more samples, Control 2 and Example 2, were prepared using the procedure of Example 1, except increasing the amount of glycine for Example 2 to 7.6%. A third sample, Example 3, was prepared by dry blending Control 2 with 8.1% of glycine and micronizing the powders. 100% of these powders passed through a 325 mesh screen. Chemical analysis of samples Control 2 and Examples 2 and 3 are summarized in Table III.

TABLE III

| Sample | % Al | % Cl | Al:Cl | Fe,ppm |
| --- | --- | --- | --- | --- |
| Control 2 | 25.27 | 17.25 | 1.92:1 | 57 |
| Example 2 | 24.22 | 16.33 | 1.93:1 | 57 |
| Example 3 | 23.1 | 15.79 | 1.92:1 | 57 |

Testing for the formation of acetaldehyde and monochlorofluoroethane was carried out as in Example 1. The samples were stored at 120° F. for 29 weeks and analyzed at intervals. The results are shown in Table IV.

TABLE IV

| | Weeks | | | | | |
| --- | --- | --- | --- | --- | --- | --- |
| | 2 | 6 | 10 | 15 | 23 | 29 |
| Acetaldehyde | | | | | | |
| Cantral 2 | 31.7 | 62.9 | 140.8 | 321.7 | 399.6 | 651.8 |
| Example 2 | 6.4 | 13.6 | 30.5 | 66.6 | 106.2 | 142.3 |
| Example 3 | 0.8 | 3.5 | 6.9 | 8.6 | 13.4 | 16.7 |
| Monachlorofluoroethane | | | | | | |
| Control 2 | 40 | 72.3 | 136.9 | 276.8 | 331.1 | 495.9 |
| Example 2 | 15.2 | 30 | 43.4 | 80.9 | 111 | 135.8 |
| Example 3 | 0.5 | 0.1 | 2 | 8.9 | 22.6 | 30.7 |

The results indicate inhibition of acetaldehyde and monochlorofluoroethane formation to be at least 93% and as high as 97–99% under extreme conditions of time and temperature. These results indicate that the inhibition rate for formation of acetaldehyde and monochlorofluoroethane is a function of the glycine concentration; and the % reduction in acetaldehyde and monochlorofluoroethane is fairly constant over 29 weeks. The FDA considers that stability of a drug product at 104° F. for 3 months is equivalent to stability for two years under ambient conditions. Antiperspirants would not be exposed to high temperatures of 120° F. continuously over time, but for only for 1–2 weeks at most.

The enhanced efficacy ACH samples of Control 2 and Example 3 were examined using high pressure liquid chromatography (HPLC) using a column 25 cm long with an ID of 6.2 mm, a pore size of 60 angstroms and a particle size of 5–7 microns. The samples were dissolved in deionized water to form a solution containing 2 weight % of aluminum. Each sample was filtered through a 0.45 micron filter and chromatographed within 5 minutes. Samples of 10 microliters were used at a flow rate of 1 ml/min, a pressure of 400–500 psig, a chart speed of 1 cm/min and using a 0.01N nitric acid eluent.

The relative retention times for Band II and Band III was 0.70–0.74 and 0.76–0.80 respectively.

Figure 1A:
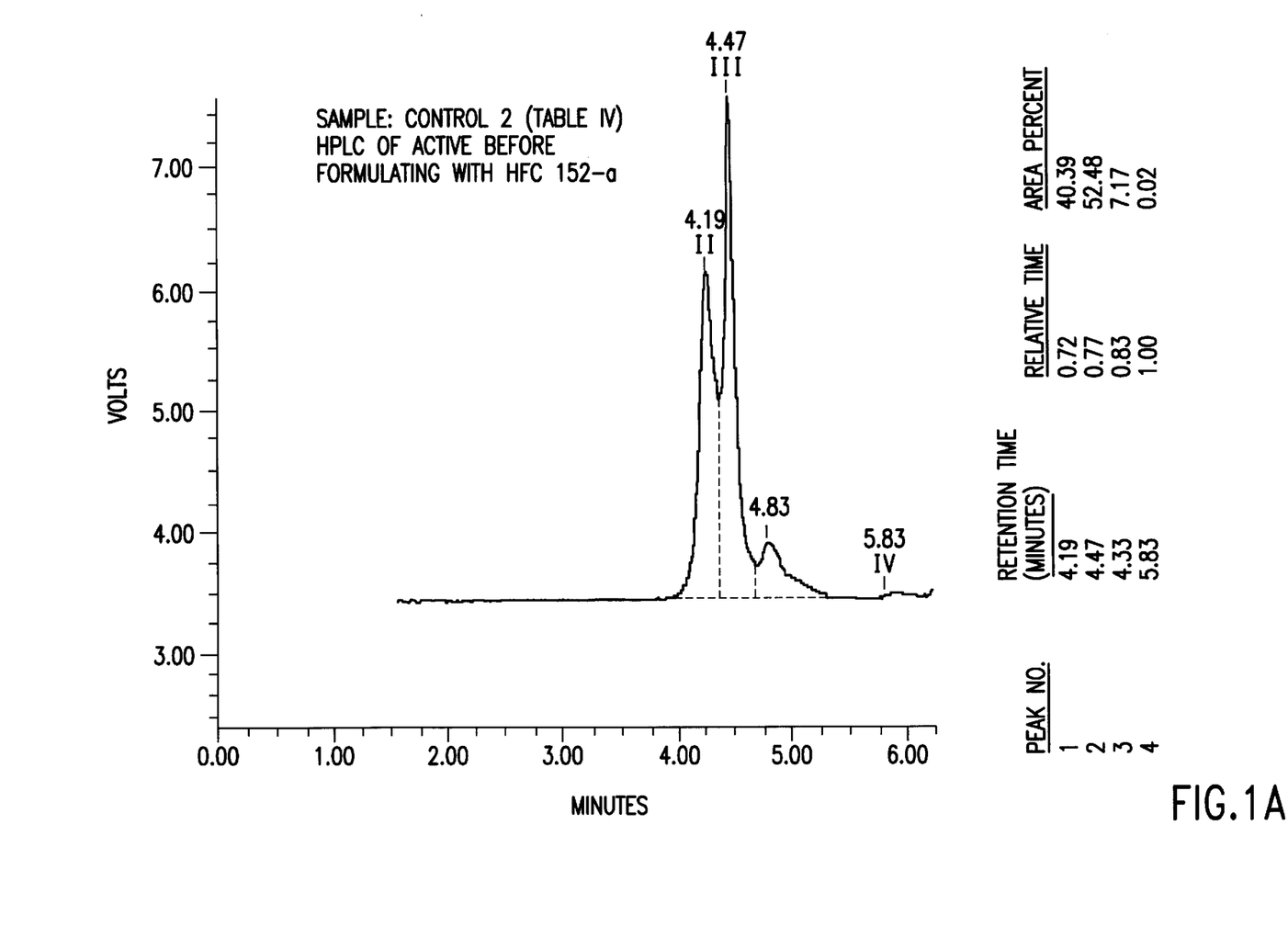
FIGS. 1A and 1B are chromatographs of a Control ACH example before and after the addition of 1,1-difluroethane.
Figure 1B:
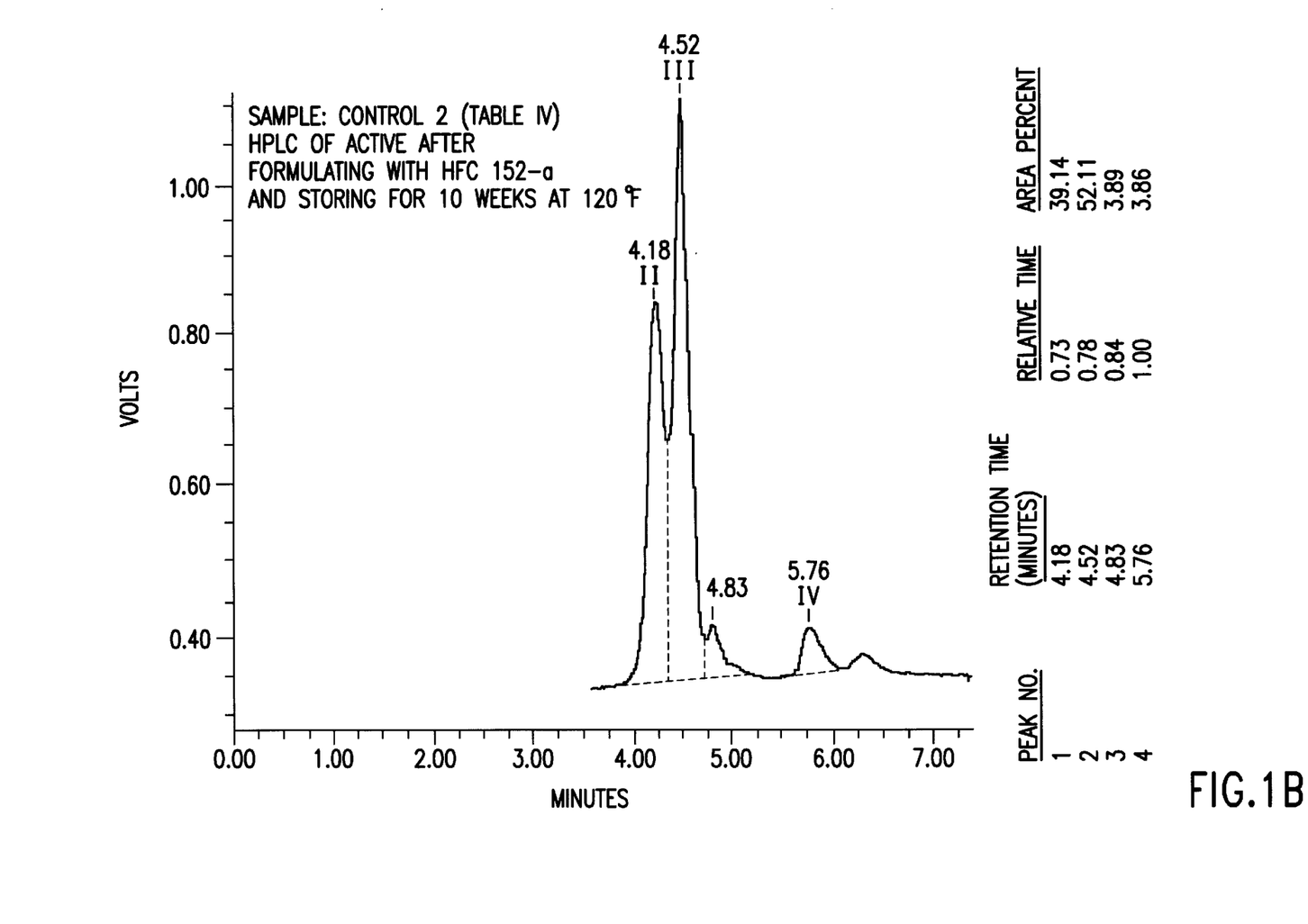
Figure 2A:
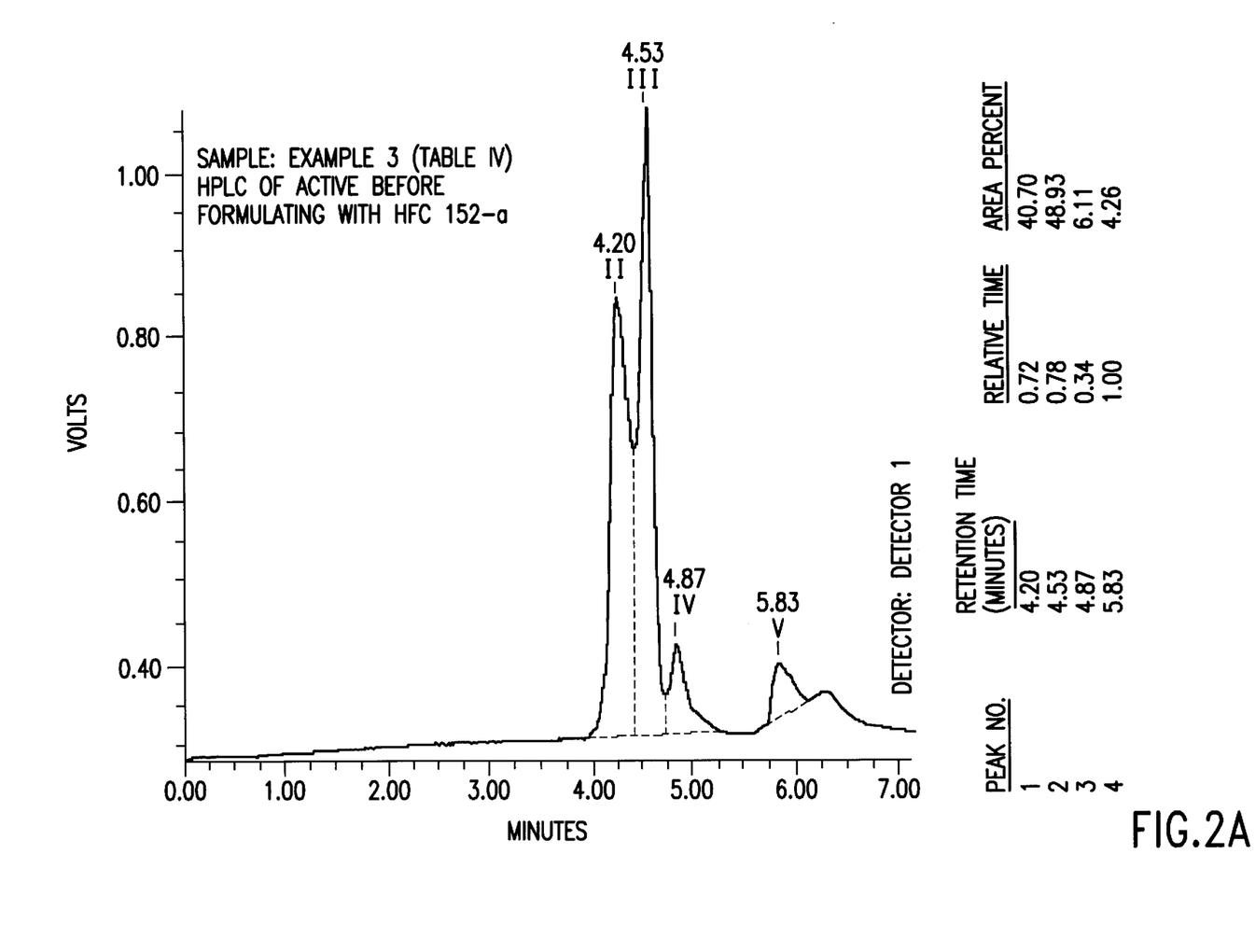
FIGS. 2A and 2B are chromatographs of a composition of the invention before and after the addition of 1,1-difluroethane.
Figure 2B:
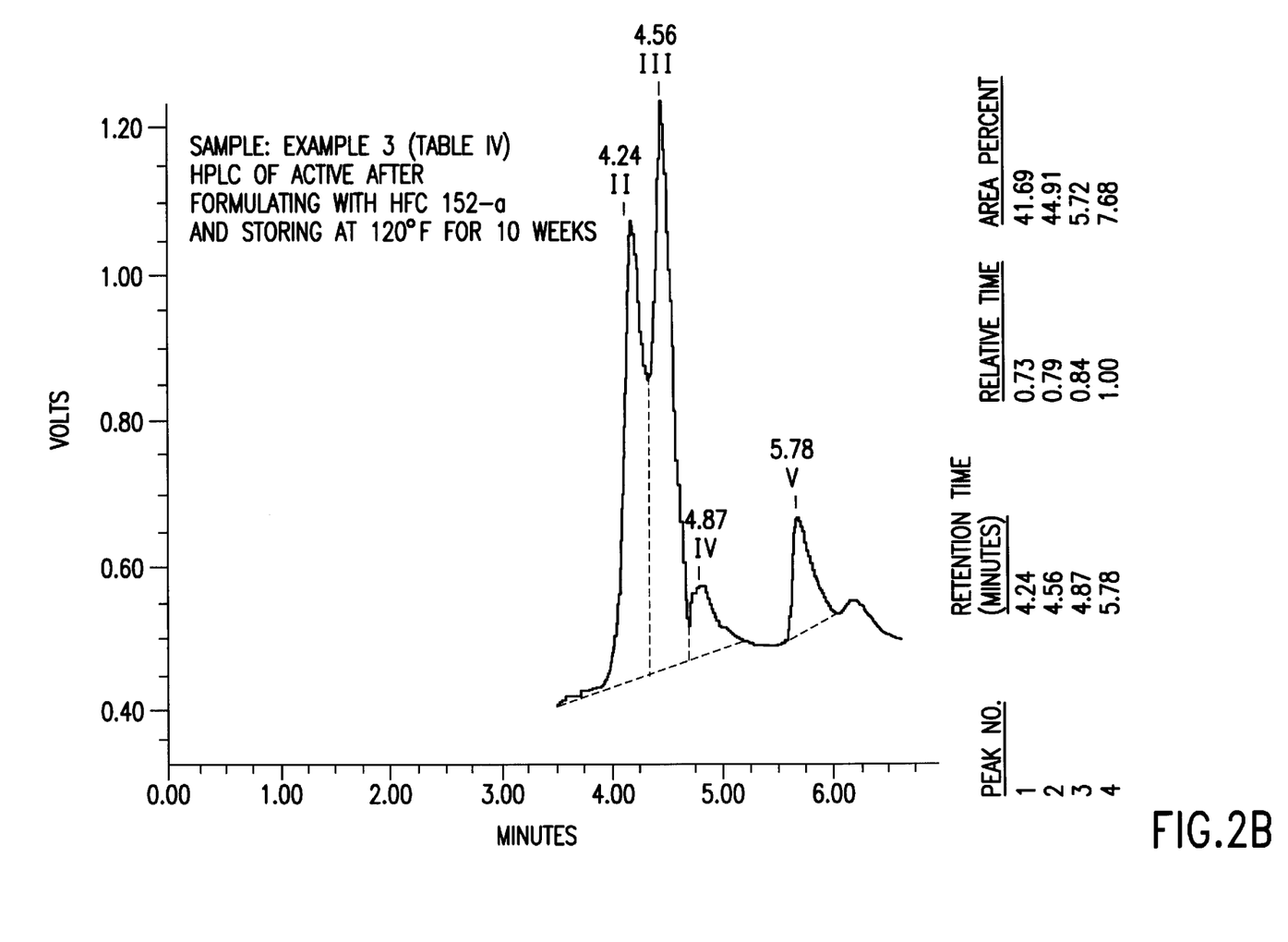

The HPLC chromatographs are shown in FIGS. 1A and 1B and 2A and 2B, respectively, wherein FIGS. 1A and 1B illustrate the Control sample before (A) and after (B) adding 1,1-difluoroethane. FIGS. 2A and 2B illustrate the Example 2 composition.

Comparison of initial HPLC and that after storage at 120° F. for 10 weeks show that the activated ACH is stable in the presence of the additive and 1,1-difluoroethane. Since there is no significant change in peak areas for Bands II and III, efficacy of the antiperspirant should remain unchanged.

Corrosion results, as shown in Table V below, show that after storage for thirteen weeks at elevated temperatures, the metal coupon in Control 2 showed detinning and rust in the vapor phase; detinning in the liquid phase; and was totally rusted in the solid phase; whereas the metal coupon in the glycine-modified ACH of Example 2 showed very very slight detinning in the vapor phase and in the liquid phase, and some detinning and slight rust in the solid phase. This is a significant improvement for can corrosion under severe storage conditions of 120° F. for 13 weeks. Thus storage at room temperature for two years should result in less or no corrosion, and the concentration of acetaldehyde and monochlorofluoroethane should be about one-half or one-third that of the concentration observed at 15 weeks.

TABLE V

| Sample | Phase | Week 6 | Week 13 |
| --- | --- | --- | --- |
| Control 2 | Vapor phase | detinning | detinning/rust |
|  | Liquid phase | detinning | detinning |
|  | Solid phase | rusted | rusted |
| Example 2 | Vapor phase | no change | very very slight detinning |
|  | Liquid phase | no change | very very slight detinning |
|  | Solid phase | slight detinning | detinning/rust |

EXAMPLES 4–5

Following the procedure of Example 1, samples were prepared by dry blending 200 grams of enhanced efficacy ACH prepared as in Example 2 with micronized hydrotalcite powder. Example 4 contained 7.87% of hydrotalcite and Example 5 contained 3.56% of glycine and 3.31% of hydrotalcite. The samples were stored at 120° F. for 12 weeks and analyzed for acetaldehyde and monochlorofluoroethane, and compared to Control 2, as shown below Table VI.

TABLE VI

|  | Weeks | | |
| --- | --- | --- | --- |
| Sample | 2 | 5 | 12 |
| Acetaldehyde |  |  |  |
| Control 2 | 8.2 | 19.9 | 42.9 |
| Example 4 | 2.6 | 6.4 | 8.7 |
| % Reduction | 75.6 | 67.8 | 79.7 |
| Example 5 | 1 | 2.2 | 3.0 |
| % Reduction | 87.8 | 88.9 | 90.9 |
| Monochlorofluoroethane |  |  |  |
| Control 2 | 49.6 | 120.6 | 250 |
| EXAMPLE 4 | 12.3 | 32.5 | 47.1 |
| % Reduction | 75.2 | 73 | 81.2 |
| Example 5 | 4 | 9.5 | 19.8 |
| % Reduction | 91.9 | 92.1 | 92.08 |

Thus the reduction for acetaldehyde and monochlorofluoroethane after 12 weeks was 79.7% and 81.2% respectively for Example 4, and 90.9 and 92.08% respectively for Example 5.

By extrapolation, it appears that at about 15% concentration, hydrotalcite alone will inhibit the generation of acetaldehyde and monochlorofluoroethane by more than 90%.

It also appears from the data that there is a synergistic effect when both glycine and hydrotalcite are blended together with ACH, (Example 5) since only 3.31% of hydrotalcite and 3.56% of glycine produced a 92% reduction in monochlorofluoroethane generation and a 90% reduction in acetaldehyde generation.

Metal coupons were tested for corrosion in the blends of Examples 4 and 5. The Control used was that of Example 2. The results are given below in Table VII.

TABLE VII

|  | Corrosion data | |
| --- | --- | --- |
| Sample | Phase | Week 12 |
| Control 2 | Vapor phase | Detinning/rust |
|  | Liquid phase | no change |
|  | Solid phase | rusted |
| Example 4 | Vapor phase | dulling |
|  | Liquid phase | detinning |
|  | Solid phase | detinning/rust |
| Example 5 | Vapor phase | no change |
|  | Liquid phase | no change |
|  | Solid phase | detinning |

Thus the control was completely rusted in the solid phase after 12 weeks, whereas the Example S blend only showed detinning after storage for 12 weeks at elevated temperature. Thus it can be concluded that an aerosol can will be able to be stored under ambient conditions for two years with minimum or no corrosion.

EXAMPLE 6

A sample blend was made from enhanced efficacy ACH and 7.2% of sodium glycinate. The blend was stored at elevated temperature for 12 weeks and compared to the Control of Example 2. The results of acetaldehyde and monochlorofluoroethane generation are given below in Table VIII.

TABLE VIII

| Sample | Weeks | | |
|---|---|---|---|
| | 2 | 5 | 12 |
| Acetaldehyde | | | |
| Control | 8.2 | 19.9 | 42.9 |
| Example 6 | 0.6 | 1.3 | 2.2 |
| % Reduction | 92.7 | 93.5 | 94.9 |
| Monochlorofluoroethane | | | |
| Control | 219.6 | 120.6 | 250 |
| Example 6 | 1.4 | 3.7 | 7.6 |
| % Reduction | 97.2 | 96.9 | 96.96 |

The above results indicate that sodium glycinate is as effective as glycine; however, sodium glycinate will neutralize part of the ACH, which may reduce its efficacy. Thus preferably the sodium salt will be used at a lower concentration in combination with glycine or hydrotalcite or a complex aluminum buffering agent.

Corrosion data is given in Table IX below.

TABLE IX

| | Corrosion after 12 weeks | |
|---|---|---|
| Control | Vapor phase | detinning/rust |
| | Liquid phase | no change |
| | Solid phase | rusted |
| Example 6 | Vapor phase | no change |
| | Liquid phase | no change |
| | Solid phase | detinning/rust |

The above data shows a significant reduction in rust. No detinning or rust was observed in the vapor or liquid phases. However, detinning and rusting was observerd in the solid phase after 12 weeks. Again, it can be concluded that no noticeable corrosion will occur after storage at room temperature or up to 70° F.

EXAMPLES 7–8

In order to test the synergistic effects of different additives of the invention, two examples were prepared by dry blending enhanced efficacy ACH with glycine, hydrotalcite and sodium glycinate in a proportion of 1:1:1 but in differing concentration. Example 7 included 10% of the additive mixture and Example 8 included 15% of the additive mixture.

Following the procedure of Example 1, the samples were stored at elevated temperature for 12 weeks. The results are given in Table X below.

TABLE X

| Sample | Weeks | |
|---|---|---|
| | 5 | 12 |
| Acetaldehyde | | |
| Example 7 | 0.8 | 1.6 |
| Example 8 | 0.6 | 1.2 |
| Monochlorofluoroethane | | |
| Example 7 | 2.9 | 7.6 |
| Example 8 | 0.9 | 2.8 |

The above results clearly show that the reaction between ACH and 1,1-difluoroethane can be controlled so that no more than a few ppm of undesirable by-products are generated, even after 12 weeks at elevated temperature.

In reality aerosol cans will be subjected to temperature cycling and will not be subjected to high temperatures on a continuous basis. This will significantly reduce the concentration of by-products because the reaction between ACH and 1,1-difluoroethane is 20 fold higher at 120° F. than at 70° F. Further, typically the concentration of ACH in aerosol cans is 10%, whereas all of the present studies were done at a worse case 16% concentration.

It can be concluded that storage under ambient conditions of the above blends will produce small or non-detectable amounts of acetaldehyde and monochlorofluoroethane.

Other approaches which can be used for stabilizing the aerosol formulation are pH adjustment of the basic aluminum chloride solution or adducts thereof with alkali salts such as sodium bicarbonate, soda ash, sodium hydroxide, potassium hydroxide and the like up to a pH of 4.6–5.0 and then spray drying the resultant basic aluminum chloride. Such an approach will have an adverse effect on the product. The use of aluminum chlorohydrate propylene glycol complex or aluminum chlorohydrate glycine complex will minimize the use of other additives such as hydrotalcite or sodium glycinate for reducing corrosion and/or inhibiting the formation of undesirable organic by-products such as acetaldehyde and monofluoroethane.

Although the invention has been described in terms of particular embodiments, blends of one or more of the various additives described herein can be used, and substitutes therefor, as will be known to those skilled in the art. Thus the invention is not meant to be limited to the details described herein, but only by the scope of the appended claims.

I claim:

1. An aerosol antiperspirant composition comprising a basic aluminum compound having the formula $Al_2(OH)_{(6-x)}Y_x$ wherein x is between 0 and 6 and y is selected from the group consisting of chloride, bromide, iodide and nitrate ions, 1,1-difluoroethane and one or more additives selected from the group consisting of an amino acid, an amino acid compound which can be an alkali metal, an alkaline earth metal, ammonium or hydroxy salt of an amino acid; a metal glycinate, a hydroxy aluminum salt of an amino acid, hydrotalcite, hydrotalcite analogues, complex aluminum buffering agents, and aluminum or magnesium based antacids and their alkali metal salts.

2. A composition according to claim 1 wherein the basic aluminum compound is enhanced efficacy aluminum chlorohydrate.

3. A composition according to claim 1 wherein the basic aluminum compound is an inorganic or organic coordinated complex of aluminum chlorohydrate.

4. A composition according to claim 1 wherein x is between 1 and 2.

5. A composition according to claim 1 wherein x is about 1.

6. A composition according to claim 1 the additive is glycine.

7. A composition according to claim 1 wherein the additive is hydrotalcite or a hydrotalcite analogue.

8. A composition according to claim 1 wherein hydrotalcite is synthetic hydrotalcite having the formula $$M^{2+}_{1-x}M^{3+}_x(OH)_2A_{x/n}{}^{n-}\cdot mH_2O$$

wherein x is greater than zero but less than or equal to 0.5; m is a positive number; $A^{n-}$ is an anion having a valence of n; $M^{2+}$ is one or more metal ions selected from the group consisting of Be, Mg, Ni, CO, Zn, Fe, Mn, Cd and Ca; and $M^{3+}$ is one or more metal ions selected from the group consisting of Al, Ga, Ni, Co, Fe, Mn, Cr and In; $A^{n-}$ is one or more anions selected from the group consisting of $SO_4^=$, OH— and $(HPO_4)$ with the proviso that when two or more anions are included, x/n is the total value for the two or more anions.

9. A composition according to claim 7 wherein the analogue has the formula: $(M_1^{2+})_{y1}[(M_2^{2+})_{y2}]_{1-x}M^{3+}_x(OH)_2$ $A_{x/n}^{n-} \cdot mH_2O$
wherein $M_1^{2+}$ is at least one divalent metal cation selected from the group consisting of Mg, Ca, Sr and Ba; $M_2^{2+}$ is at least one divalent metal cation selected from the group consisting of Zn, Cd, Pb and Sn; $M^{3+}$ is a trivalent metal cation; $A^{n-}$ is an anion having a valence of n; and x, $y_1$, $y_2$ and m are positive numbers having the following values: x is greater than zero and less than 0.5; $y_1$ and $y_2$ are greater than zero; $(y_1+y_2)$ is greater than 0.5 and less than 1 and m is greater than zero and less than 2.

10. A composition according to claim 1 wherein the additive is sodium or zinc glycinate.

11. A composition according to claim 1 wherein the hydroxy salt is an aluminum-magnesium-hydroxy glycine compound.

12. A composition according to claim 11 wherein the aluminum-magnesium-hydroxy glycine compound is selected from the group consisting of monohydroxy aluminum, aluminum glycinate, magnesium glycinate and calcium glycinate.

13. A composition according to claim 1 wherein the complex aluminum buffering agent is selected from the group consisting of aluminum hydroxy carbonate, magnesium hydroxide and aluminum compounds containing two or more of the group consisting of magnesium, calcium, nickel, carbonate, sulfate, hydroxy and water.

14. A composition according to claim 13 wherein the aluminum buffering agent contains magnesium and carbonate.

15. A composition according to claim 1 wherein the complex aluminum buffer contains aluminum hydroxide and one or more of magnesium carbonate, calcium carbonate, dihydroxy aluminum sodium carbonate, tetrahydroxy dialuminum magnesium carbonate, hydrated magnesium aluminate, hydrated magnesium aluminum sulfate, aluminum magnesium hydroxy sulfate, aluminum hydroxy carbonate and magnesium hydroxide.

16. A composition according to claim 1 wherein the additive is a mixture of glycine and hydrotalcite or a hydrotalcite analogue.

17. A composition according to claim 1 wherein the additive is a mixture of glycine, hydrotalcite and sodium glycinate.

18. A composition according to claim 1 wherein from about 0.5 to 15% by weight of the antiperspirant of the additive is present.

19. A composition according to claim 1 wherein sufficient additive is present in the antiperspirant composition to prevent can corrosion for at least two years at ambient conditions.

* * * * *